United States Patent [19]

Fiala

[11] Patent Number: Plant 7,216

[45] Date of Patent: Apr. 10, 1990

[54] FLOWERING CRAB APPLE TREE

[75] Inventor: John L. Fiala, Medina, Ohio

[73] Assignee: J. Frank Schmidt & Son Co., Boring, Oreg.

[21] Appl. No.: 183,708

[22] Filed: Apr. 19, 1988

[51] Int. Cl.[4] ..... A01H 5/00

[52] U.S. Cl. ..... Plt./34

[58] Field of Search ..... Plt./34

*Primary Examiner*—Robert E. Bagwill

*Attorney, Agent, or Firm*—Klarquist, Sparkman, Campbell, Leigh & Whinston

[57] ABSTRACT

A new variety of crab apple tree, which I call "Doubloons", has large white double flowers, a generally round habit of growth with upright spreading dense branches and yellow fruit. The new variety is resistant to apple scab.

1 Drawing Sheet

DESCRIPTION

The present invention relates to a new and distinct variety of flowering crab apple tree which I have named Doubloons.

My new variety originated out of a breeding program as a cross of Malus 'Spring Song'×(M. 'Dorothea'×M. 'Wintergold'). My attention was first directed to this plant because it combined disease resistant foliage with large, double, white flowers. In comparison, other crab apple trees of the same species growing in the same area were moderately or severely susceptible to apple scab. My new variety exhibited good resistance to this disease. In addition, the flowers of my new variety appeared large in comparison to other cultivars having double or semi-double white or pinkish white flowers.

I observed my new variety for a number of years growing in a cultivated area on my Falconskeape farm in Medina, Ohio. My observations have confirmed that my variety is a distinct and unusual cultivar. Subsequent asexual propagation of my variety by budding under my direction at the nursery of J. Frank Schmidt & Son Co. in Boring, Oreg., and observation of the resulting progeny has proven the characteristics of my new variety to be fixed. Furthermore, these observations have confirmed that my new variety represents a new and improved variety of flowering crab apple tree, as particularly evidenced by the following unique combination of characteristics, which have proven firmly fixed, are outstanding therein, and which distinguish it from all other varieties of this species of which I am aware:

1. Generally rounded habit of growth with upright spreading dense branches;
2. Large white blooms which are fully double;
3. Yellow fruit; and
4. High resistance to apple scab.

The accompanying photographs depict the color and size of the blooms and fruit of my variety, as well as the shape of the tree, as nearly true as is reasonably possible to make the same in a color illustration of this character.

FIG. 1 is a color photograph of flowers of the tree of the present invention;

FIG. 2 is a color photograph of a tree of the present invention generally showing its rounded form and dense upright branches; and FIG. 3 is a color photograph of fruit on the tree of the present invention.

The blooms of my malus "Doubloons" variety differ from those of its parent cultivars in the following manner:

"Spring Song"—Flowers are single, white

"Wintergold"—Flowers are single, white

"Dorothea"—Flowers are rose pink to crimson, double.

The following comparison chart shows how my new variety of tree differs in some respects from other flowering crab apple cultivars having double or semi-double white or pinkish white flowers:

| Cultivar | Feature of Cited Cultivar | Feature of My New Variety |
|---|---|---|
| Angel Choir | Fruit - Red | Yellow |
| Blanche Ames | Branches - Horizontal to Pendulous | Upright |
| | Petals - Narrow | Broad |
| | Scab - Susceptible | Resistant |
| Bridal Crown | Fruit - Red, 1.3 cm | Yellow 0.9–1.0 cm |
| Charlotte | Fruit - green, 2.5–4.0 cm | Yellow 0.9–1.0 cm |
| Chinese Double Flwg. | Fruit - 2.0–3.0 cm | 0.9–1.0 cm |
| Egret | Fruit - Red | Yellow |
| | Habit - Weeping | Upright |
| Katherine | Fruit - Greenish Yellow | Yellow |
| | Scab - Very Susceptable | Resistant |
| Madonna | Fruit - blushed red | Yellow |
| | Flowerbuds - white | Crimson |
| Snowcloud | Fruit - 1.2–1.4 cm | 0.9–1.0 cm |
| | - Sparsely Produced | Abundant |
| | Scab - Susceptible | Resistant |
| Scheideckeri | Fruit - 1.3–2.0 cm | 0.9–1.0 cm |
| | Scab - Susceptible | Resistant |
| Sieholdi | Fruit - Orange, 1.3 cm | Yellow |
| Fuji | | 0.9–1.0 cm |
| Van Eseltine | Fruit - Yellow - Carmine Cheeks | Yellow |
| | - 1.6–2.0 cm | 0.9–1.0 cm |
| | angular shape | Round |
| | Scab - Susceptible | Resistant |

The following is a detailed description of my new variety of Malus "Doubloons" flowering crab apple tree, with color terminology in accordance with The Royal Horticultural Society Colour Chart (hereinafter RHS), published by The Royal Horticultural Society of London.

Parentage: Malus "Spring Song"×(M. "Dorothea"×M. "Wintergold").

Propagation: Holds to distinguishing characteristics through succeeding propagation by budding.

Locality where grown and observed: Medina, Ohio and Boring, Oreg.

Tree: Rounded with upright spreading branches, dense.

Foliage:

*Size.*—6.0–8.0 cm long × 3.5–4.0 cm wide.

*Shape.*—Ovate.

*Apex.*—Accuminate.

*Base.*—Broadly wedge-shaped.

*Margin.*—Serrate.

*Color.*—RHS Green 137A to 139A; fall color yellow 13B.

Buds: RHS Red 53C in tight bud stage becoming Red 54A to 54B as they begin to open.

Blooms:

*Character.*—Fully double with 10–15 petals.

*Size.*—3.5–4 cm diameter.

*Color.*—white.

Fruit:

*Shape.*—Round.

*Size.*—0.9–1.0 cm in diameter.

*Quantity.*—Abundant.

*Color.*—Yellow RHS 13B to 15B.

*Persistence.*—Moderate, varies with weather and locality, but usually until mid-November.

I claim:

1. A new and distinct variety of flowering crab apple tree substantially as herein shown and described, characterized particularly as to novelty by its large, white, double flowers and yellow fruit.

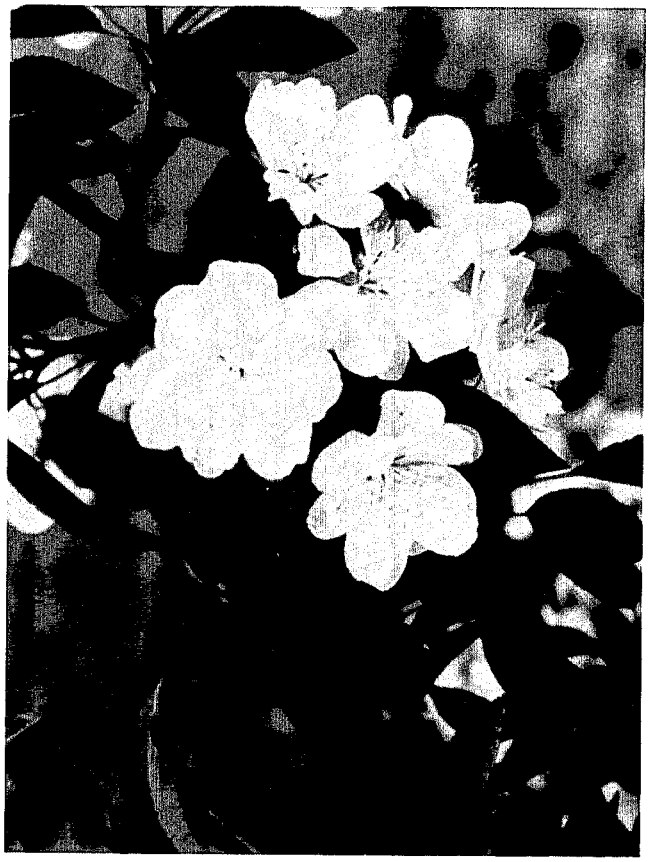
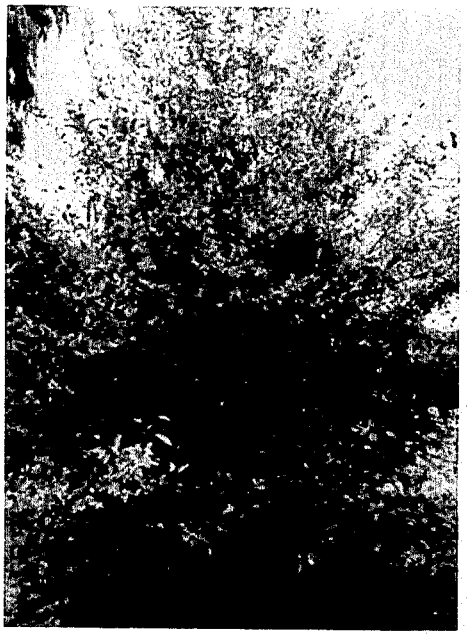
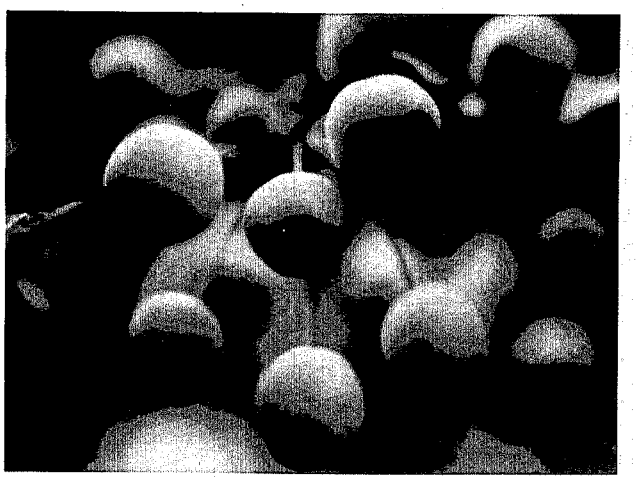

* * * * *